(12) United States Patent
Ahn et al.

(10) Patent No.: US 11,771,315 B2
(45) Date of Patent: Oct. 3, 2023

(54) MOBILE COLPOSCOPY DEVICE FOR EARLY DIAGNOSIS OF CERVICAL CANCER

(71) Applicants: Pukyong National University Industry—University Cooperation Foundation, Busan (KR); KOSIN UNIVERSITY INDUSTRY—ACADEMY COOPERATION, Busan (KR)

(72) Inventors: Yeh-Chan Ahn, Busan (KR); Daa Young Kwon, Busan (KR); Yi Keun Kim, Busan (KR); Chul Ho Oak, Busan (KR); Hang Goo Yun, Busan (KR); Sung Won Kim, Busan (KR)

(73) Assignees: Pukyong National University Industry—University Cooperation Foundation, Busan (KR); KOSIN UNIVERSITY INDUSTRY—ACADEMY COOPERATION, Busan (KR)

( * ) Notice: Subject to any disclaimer, the term of this patent is extended or adjusted under 35 U.S.C. 154(b) by 97 days.

(21) Appl. No.: 17/481,093

(22) Filed: Sep. 21, 2021

(65) Prior Publication Data
US 2022/0087520 A1 Mar. 24, 2022

(30) Foreign Application Priority Data
Sep. 21, 2020 (KR) .......................... 10-2020-0121249

(51) Int. Cl.
*A61B 1/303* (2006.01)
*A61B 1/04* (2006.01)
(Continued)

(52) U.S. Cl.
CPC ................. *A61B 1/303* (2013.01); *A61B 1/04* (2013.01); *A61B 1/07* (2013.01); *A61B 1/32* (2013.01)

(58) Field of Classification Search
CPC .. A61B 1/303; A61B 1/04; A61B 1/07; A61B 1/32; A61B 1/00073;
(Continued)

(56) References Cited

U.S. PATENT DOCUMENTS

2005/0277811 A1* 12/2005 Richards ............ A61B 1/00105
600/184
2008/0130108 A1* 6/2008 Bayer ...................... A61B 1/05
359/489.07

(Continued)

*Primary Examiner* — Michael J Carey
*Assistant Examiner* — Christen A. Sharpless
(74) *Attorney, Agent, or Firm* — Studebaker & Brackett PC

(57) ABSTRACT

Disclosed is a mobile colposcopy device for early diagnosis of cervical cancer, which includes an insertion unit which is inserted into the vagina of a woman, has a penetrating hole formed in one end coming into contact with the uterus, and is provided with a capturing path communicating with the penetrating hole, a capturing unit which is provided in the insertion unit so as to capture the cervix through the capturing path, and a lighting unit which is provided on the capturing path of the insertion unit and irradiates a lighting to the cervix through the penetrating hole. According to the present disclosure, the mobile colposcopy device for early diagnosis of cervical cancer can be simply and easily used so as to perform cervical cancer screening using a mobile colposcopy without environmental constraints including hospitals and allows women to early diagnose cervical cancer.

12 Claims, 6 Drawing Sheets

(51) Int. Cl.
*A61B 1/07* (2006.01)
*A61B 1/32* (2006.01)

(58) Field of Classification Search
CPC ..... A61B 1/00052; A61B 1/015; A61B 1/042; A61B 1/00179; A61B 1/0669; A61B 1/00105
See application file for complete search history.

(56) References Cited

U.S. PATENT DOCUMENTS

| | | | |
|---|---|---|---|
| 2016/0248951 A1* | 8/2016 | Fletcher | A61B 5/0077 |
| 2016/0287063 A1* | 10/2016 | Ramanujam | A61B 1/00087 |
| 2017/0055811 A1* | 3/2017 | Germain | A61B 18/1482 |
| 2020/0107714 A1* | 4/2020 | Bar-Or | A61B 1/00066 |

* cited by examiner

MOBILE COLPOSCOPY DEVICE FOR EARLY DIAGNOSIS OF CERVICAL CANCER

CROSS-REFERENCE TO RELATED APPLICATIONS

This application claims the priority of Korean Patent Application No. 10-2020-0121249 filed on Sep. 21, 2020, in the Korean Intellectual Property Office, the disclosure of which is incorporated herein by reference.

BACKGROUND OF THE INVENTION

Field of the Invention

The present disclosure relates to a mobile colposcopy device for early diagnosis of cervical cancer, and more specifically, to a mobile colposcopy device for early diagnosis of cervical cancer capable of simply performing cervical cancer screening visually using a mobile colposcopy without environmental constraints including hospitals.

Description of the Related Art

Cervical cancer is the second most common cancer worldwide in women, and 23% of total women cancer is uterine cancer, and cervical cancer accounts for 90 to 95% of the uterine cancer.

Such a cervical cancer has good treatment and prognosis in early detection (precancer stage), but since the survival rate is degraded within five years in progressing to cancer, women need to receive cervical cancer screening at one-year intervals so as to early find the cervical cancer above all.

Currently, in cervical cancer screening, there are treatment methods such as local destruction and surgery therapies, chemical and radiation therapies, and the like as well as diagnosis methods such as cytologic smear, colposcopy, biopsy, and the like. Recently, a self-diagnostic kit and like, which can perform a self-female disease test, have been released.

Representatively, a colposcopy used for screening is a screening method capable of performing biopsy or treatment on suspicious areas while observing the cervix through a specially designed enlarged lens and identifying directly various abnormal symptoms of the cervix with eyes according to a series of diagnostic criteria. In developed countries, there is a high accessibility, but in the case of developing countries such as Asia, South America, and Africa, where about 80% of cervical cancer occurs, there is a problem that the early diagnosis of cervical cancer is difficult due to a tooling problem.

The above-described technical configuration is the background art for helping in the understanding of the present invention, and does not mean a conventional technology widely known in the art to which the present invention pertains.

SUMMARY OF THE INVENTION

The present disclosure is conceived to improve the above problems, and an object of the present disclosure is to provide a mobile colposcopy device for early diagnosis of cervical cancer capable of early diagnosing cervical cancer using a relatively easy-equipped device such as a smartphone attached with a capturing camera for early diagnosis of cervical cancer.

According to an aspect of the present disclosure, there is provided a mobile colposcopy device for early diagnosis of cervical cancer, which includes an insertion unit which is inserted into the vagina of a woman, has a penetrating hole formed in one end coming into contact with the uterus, and is provided with a capturing path communicating with the penetrating hole, a capturing unit which is provided in the insertion unit so as to capture the cervix through the capturing path, and a lighting unit which is provided on the capturing path of the insertion unit and irradiates a lighting to the cervix through the penetrating hole.

The insertion unit may be formed with an inlet so as to communicate with the capturing path to prevent condensation from occurring on the capturing unit and to circulate air on the capturing path to the outside or inject a test solution during the screening of the cervix.

The lighting unit may include a light source which is provided in the insertion unit to irradiate a lighting on the capturing path; and a light guide which induces the lighting generated in the light source in a direction of the penetrating hole.

The mobile colposcopy device may further include an optical unit which is provided on the capturing path and blocks reflection light which is reflected on the surface of a cervical tissue to be introduced to the penetrating hole and transmits only a lighting which is reflected to the penetrating hole from an inside of the cervical tissue by passing through the surface of the cervical tissue.

The capturing unit may hold a smartphone provided with a capturing camera, and support the smartphone so that the capturing camera faces the penetrating hole so that the capturing camera captures the cervix through the penetrating hole.

An insertion space may be provided at the other end of the insertion unit and formed so that the smartphone is inserted, but may be formed with a setting port in which a capturing lens of the capturing camera is set at a position facing the penetrating hole.

The capturing unit may be any one of an endoscope camera and a hyperspectral camera.

The penetrating hole may be inclined at a predetermined angle based on a longitudinal center line of the capturing path.

The mobile colposcopy device may further include an extension unit which extends a space in the vagina when the insertion unit is inserted into the vagina.

The extension unit may have a hollow so that an end of the insertion unit may be inserted, but include a first extension member and a second extension member which are supported to each other to be rotatable with each other so that be far from the center of the hollow; and a plurality of handles which are formed in the extension unit and held by an operator to rotate the extension members.

The insertion unit may have a guide groove extended in a predetermined length along an insertion direction to the vagina, and the extension unit may have a guide protrusion formed on any one of the first extension member and the second extension member so as to be inserted to the guide groove.

The insertion unit may have an inner diameter which is tapered to be closer to the penetrating hole so that scattering light output from the light source and scattered by an inner wall surface is incident to the cervical tissue.

The optical unit may consist of a linear polarizer (LP) which is provided on the capturing path and forms a parallel polarization (P-polarization) of light output from the light source and a $1/4\lambda$ retarder (QWP) which is provided behind the linear polarizer based on an output direction of the light on the capturing path to form light passing through the linear polarizer to a left circular polarization.

The insertion unit may further include a communication unit which communicates with the inlet and is formed in a circumferential direction along an inner circumferential direction of the insertion unit, and at least one ejection pipe which is extended to the penetrating hole side along the capturing path from the communication unit and has an outlet so that external air introduced through the inlet is ejected to an end of the penetrating hole or a test solution is ejected to the penetrating hole side.

According to the present disclosure, the mobile colposcopy device for early diagnosis of cervical cancer can be simply and easily used so as to perform cervical cancer screening using a mobile colposcopy without environmental constraints including hospitals and allow women to early diagnose cervical cancer.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
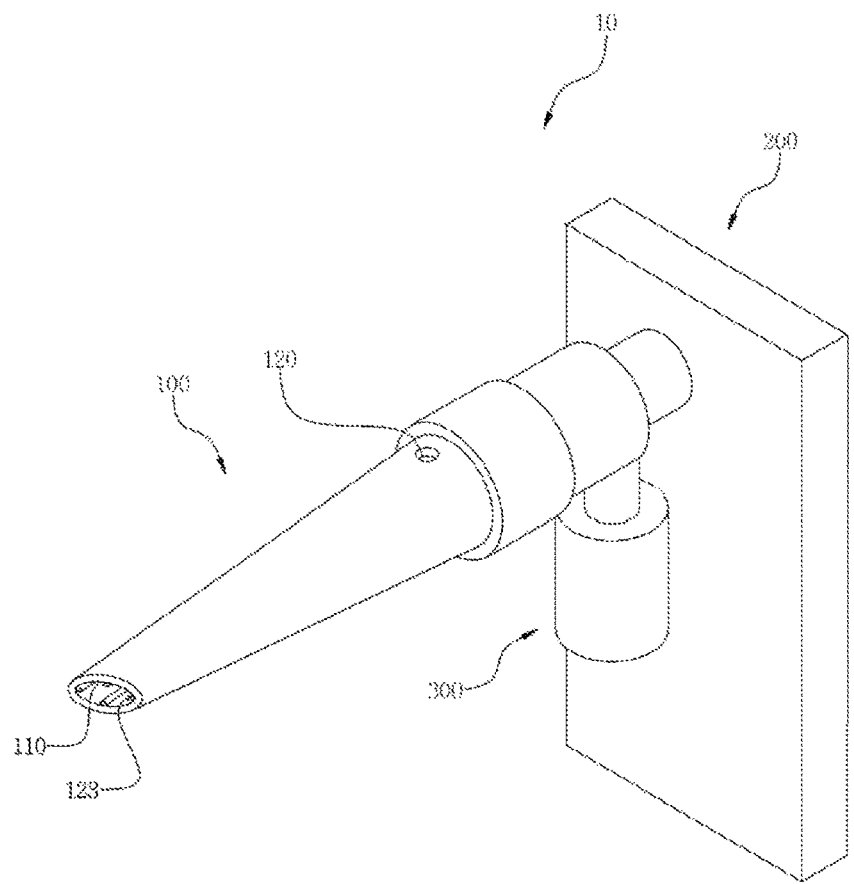
FIG. 1 is a perspective view illustrating a first embodiment of a mobile colposcopy device for early diagnosis of cervical cancer according to the present disclosure.

Hereinafter, a mobile colposcopy device 10 for early diagnosis of cervical cancer according to an embodiment of the present disclosure will be described in detail with reference to the accompanying drawings. The present disclosure may have various modifications and various embodiments, and specific embodiments will be illustrated in the drawings and described in detail in the specification. However, this does not limit the present disclosure to specific exemplary embodiments, and it should be understood that the present disclosure covers all modifications, equivalents and replacements included within the idea and technical scope of the present disclosure. In describing each drawing, like reference numerals were used for like components. With respect to the accompanying drawings, the dimensions of the structures are exaggerated for the clarity of the present disclosure.

Terms such as first, second, and the like may be used for describing various components, but the components are not limited by the terms. The terms are used only to discriminate one component from the other component. For example, without departing from the scope of the present disclosure, a first component may be referred to as a second component, and similarly, the second component may also be referred to as the first component.

The terminology used herein is used for describing specific embodiments only and is not intended to limit the present disclosure. A singular form may include a plural form unless otherwise clearly indicated in the context. In the present application, it should be understood that term "including" or "having" indicates that a feature, a number, a step, an operation, a component, a part or the combination thereof described in the specification is present, but does not exclude a possibility of presence or addition of one or more other features, numbers, steps, operations, components, parts or combinations thereof, in advance.

Unless otherwise contrarily defined, all terms including technological or scientific terms used herein have the same meanings as those generally understood by those skilled in the art. Terms defined in a generally used dictionary should be interpreted to have the same meaning as the meaning in the context of the related arts, and are not interpreted as an ideal meaning or excessively formal meanings unless otherwise clearly defined in the present application.

Figure 2:
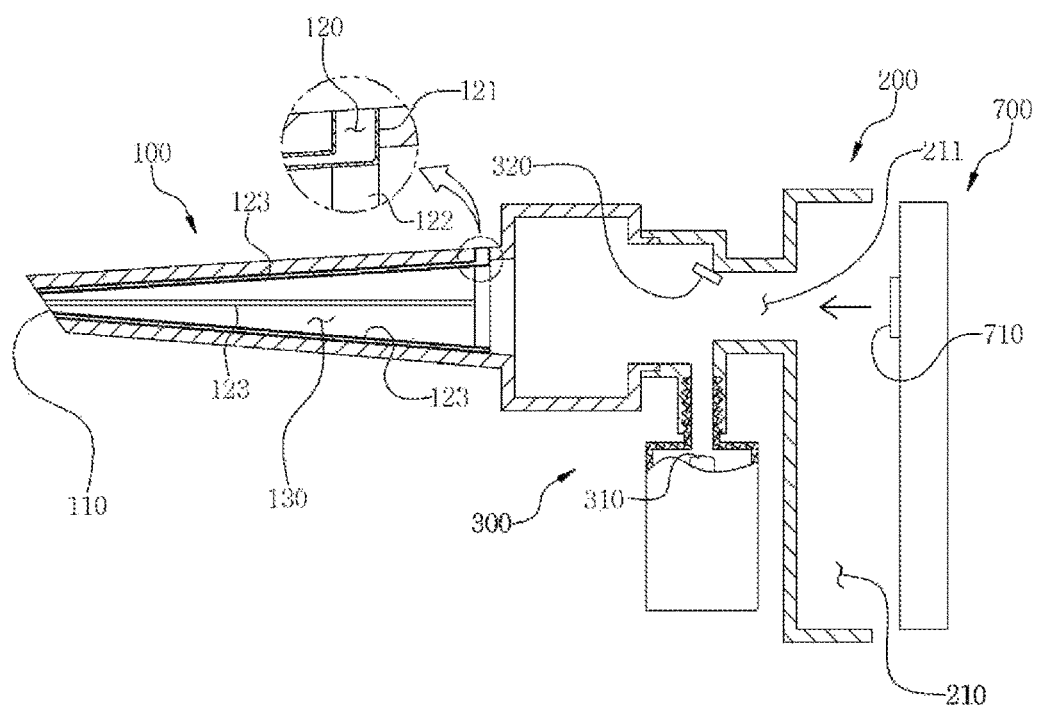
FIG. 2 is a cross-sectional view illustrating an internal structure of the mobile colposcopy device for early diagnosis of cervical cancer of FIG. 1.

FIGS. 1 to 2 illustrate a first embodiment of a mobile colposcopy device 10 for early diagnosis of cervical cancer according to the present disclosure.

Referring to FIGS. 1 to 2, the mobile colposcopy device 10 for the early diagnosis of cervical cancer includes an insertion unit 100, a capturing unit 200 and a lighting unit 300.

The insertion unit 100 is inserted into the vagina of a woman, has a penetrating hole 110 formed at one end coming into contact with the uterus, and is provided with a capturing path 130 communicating with the penetrating hole 110 therein.

The capturing path 130 extends forward and backward, and a rear portion of the insertion unit 100 is opened to communicate with the capturing unit 200.

At this time, the insertion unit 100 is formed in a tapered shape in which an inner diameter is decreased toward the penetrating hole 110 in the capturing unit 200, so that an examiner easily inserts the insertion unit 100 into the vagina. Further, in the shape of the tapered insertion unit 100, the inner diameter of the capturing path 130 is decreased so that a lighting irradiated from the lighting unit 300 is not directly illuminated to be an indirect lighting by scattering light so that light reflected on the surface of the cervical tissue is reduced.

The penetrating hole 110 is inclined at a predetermined angle based on a longitudinal centerline of the capturing path 130. It is preferable that the examiner screens the cervix by contacting the inclined penetrating hole 110 with the cervix.

The penetrating hole 110 inclined at the predetermined angle secures the capturing path 130 by pushing a cervical tissue 900 interfering with the capturing path 130 by the inclined portion of the penetrating hole 110 when screening the cervix formed differently for each person due to an individual anatomical difference.

Further, the insertion unit 100 has an inlet 120 formed on an outer circumferential surface to communicate with the capturing path 130.

Air is circulated to the outside through the inlet 120 on the capturing path 130 to prevent condensation from occurring on the capturing unit 200. When the condensation occurs on the capturing unit 200, air flowing into the inlet 120 from the outside may be circulated to be discharged through the penetrating hole 110 inclined at the predetermined angle.

The position and the size of the inlet 120 are not limited.

The capturing unit 200 holds a smartphone 700 provided with a capturing camera 710 and the capturing unit 200 is provided at the rear end of the insertion unit 100 to hole the smartphone 700 having the capturing camera 710. The capturing unit 200 has an insertion space 210 formed on the rear surface so that the smartphone 700 may be inserted. The insertion space 210 is formed to correspond to a cross-sectional area of the smartphone 700 so that the smartphone 700 is forcibly fitted.

The insertion space 210 is formed with a setting port 211 in which a capturing lens of the capturing camera 710 provided in the smartphone 700 may be set at a position facing the penetrating hole 110 on the rear surface of the capturing unit 200.

The setting port 211 is formed at the position facing the penetrating hole 110 and is formed with an area corresponding to the lens of the capturing camera 710 so that the lens of the capturing camera 710 of the smartphone 700 may be inserted.

At this time, the capturing unit 200 supports the smartphone 700 so that the capturing camera 710 faces the penetrating hole 110 so that the capturing camera 710 may capture the cervix through the penetrating hole 110.

Although not illustrated, the capturing unit 200 includes a first adjustment member, a second adjustment member, and a spring member.

When the smartphone 700 is inserted in the insertion space 210, the smartphone 700 is seated on the first adjustment member, and the second adjustment member can be adjusted with the length and the width by the spring member to fix the smartphone 700 seated on the first adjustment member.

The lighting unit 300 includes a light source 310 and a light guide 320.

The light source 310 is provided below the insertion unit 100 to irradiate a lighting on the capturing path 130.

The light guide 320 is provided inside the insertion unit 100 to induce the lighting generated in the light source 310 in a direction of the penetrating hole 110.

The light guide 320 is provided on an inner wall surface of the insertion unit 100 facing the light source 310 and applied with a reflection mirror capable of reflecting the light generated from the light source 310 to the penetrating hole 110 side.

Meanwhile, although not illustrated, since one end is installed in the light source 310 and the other end is installed in the insertion unit 100, but installed to face the penetrating hole 110, the light guide 320 may also be applied with an optical fiber to be transmitted to the penetrating hole 110 by waveguiding the light generated from the light source 310.

At this time, a plurality of optical fibers is provided and one end is bonded to a bundle to be connected to the light source 310. It is preferred that the other ends of the optical fibers are dispersed and inserted to the inside the insertion unit 100 to be spaced apart from each other and disposed to face the penetrating hole 110.

When the light emitted from the light source 310 is input to one end of the optical fiber, a second optical coupler such as a lens may also be used. The light input to an end of the optical fiber is transmitted to the other end along the optical fiber to be emitted to the penetrating hole 110 side.

The insertion unit 100 may allow the penetrating hole 110 to be in complete contact with the surface of the cervix so as to prevent the introduction of an external lighting such as a fluorescent light. That is, only a desired lighting of the lighting unit 300 is irradiated to the cervix so that conditions of the lighting irradiated to the capturing of the cervix are uniform.

As such, an image acquired while the same capturing conditions are always uniformly maintained has an effect so as to reduce the distortion during disease stage analysis using artificial intelligence in the future.

In the first embodiment, the insertion unit 100, the capturing unit 200, and the lighting unit 300 may be produced by 3D printing to be more easily manufactured and used.

Figure 3:
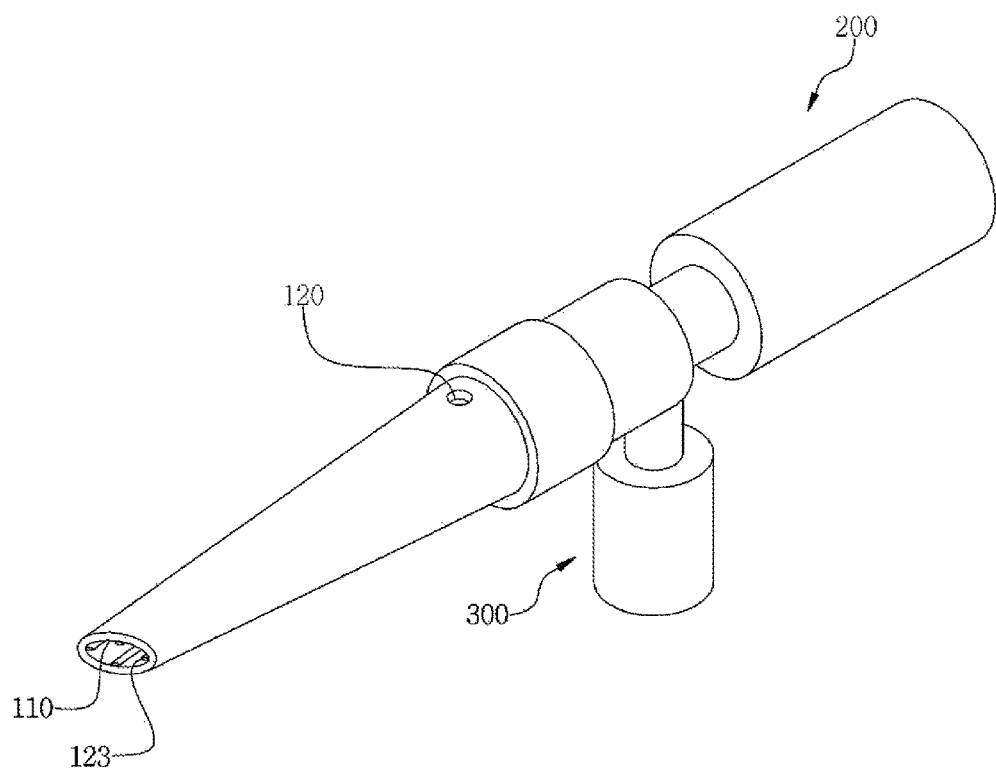
FIG. 3 is a perspective view illustrating a second embodiment of a mobile colposcopy device for early diagnosis of cervical cancer.
Figure 4:
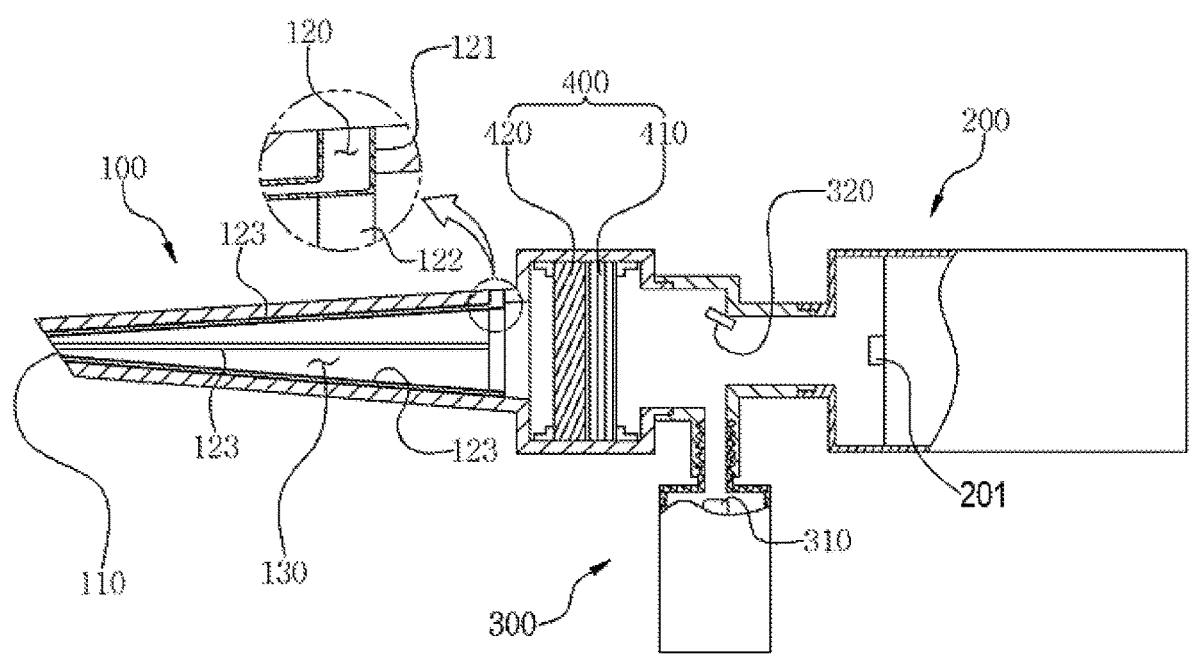
FIG. 4 is a cross-sectional view illustrating an internal structure of the mobile colposcopy device for early diagnosis of cervical cancer of FIG. 3.

FIGS. 3 to 4 illustrate a mobile colposcopy device 10 for early diagnosis of cervical cancer according to a second embodiment.

Elements having the same function as the drawings illustrated above are denoted by the same reference numerals.

Referring to FIGS. 3 to 4, the capturing unit 200 is provided at the rear end of the insertion unit 100 facing the penetrating hole 110 so that an endoscope camera facing the penetrating hole 110 is applied. The mobile colposcopy device 10 for early diagnosis of cervical cancer further includes the optical unit 400 provided on the capturing path 130.

Figure 9:
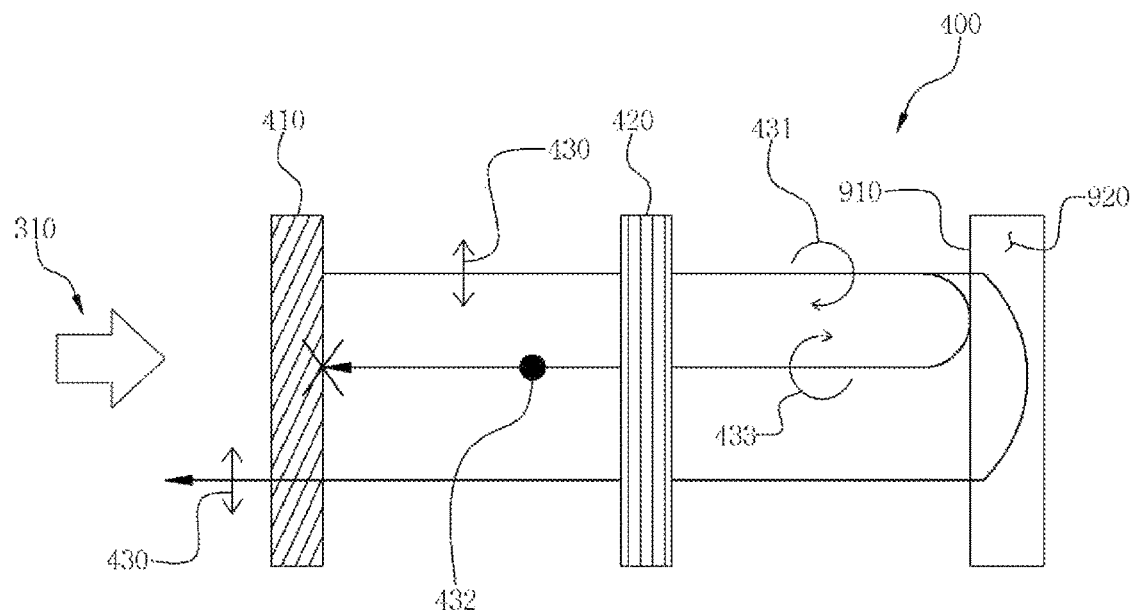
FIG. 9 is a schematic view illustrating a principle of an optical unit of the second embodiment of the mobile colposcopy device for early diagnosis of cervical cancer.

FIG. 9 illustrates a principle of a polarization system of the optical unit 400 according to the second embodiment.

The optical unit 400 may block reflection light which is reflected on a surface 910 of the cervical tissue 900 to be introduced to the penetrating hole 110 and transmit only a lighting which is reflected to the penetrating hole 110 from an inside 920 of the cervical tissue 900 by passing through the surface 910 of the cervical tissue 900.

The optical unit 400 consists of a linear polarizer 410 and a 1/4λ retarder 420.

The linear polarizer 410 is first provided on the capturing path 130 and forms a parallel polarization 430 of light output from the light source 310.

The 1/4λ retarder 420 is provided behind the linear polarizer 410 based on an output direction of the light on the capturing path to form light passing through the linear polarizer 410 to a left circular polarization 431.

Non-polarized light emitted from the light source 310 passes through the linear polarizer 410 to form a parallel polarization 430 and the light with the parallel polarization 430 passes through the 1/4λ retarder 420 to form a left circular polarization 431.

The light regularly reflected on the surface 910 of the cervical tissue 900 to be returned forms a right circular polarization 433 and the light with the right circular polarization 433 passes through the 1/4λ retarder 420 to form a vertical polarization 432 and does not pass through the linear polarizer 410 so as not to reach the capturing unit 200.

On the other hand, when the light passing through the linear polarizer 410 and the 1/4λ retarder 420 is equally reflected on an inside 920 of the cervical tissue 900, the reflected light first passes through the 1/4λ retarder 420 by including information of the inside 920 of the cervical tissue 900 and passes through the linear polarizer 410 to reach the capturing unit 200 as the light with the parallel polarization 430.

As a result, the light reflected on the surface 910 of the cervical tissue 900 does not enter the capturing unit 200 and only the remaining light reflected on the inside 920 of the cervical tissue 900 passes through the capturing unit 200, thereby removing surface reflection interfering with the data analysis and diagnosis.

Figure 5:
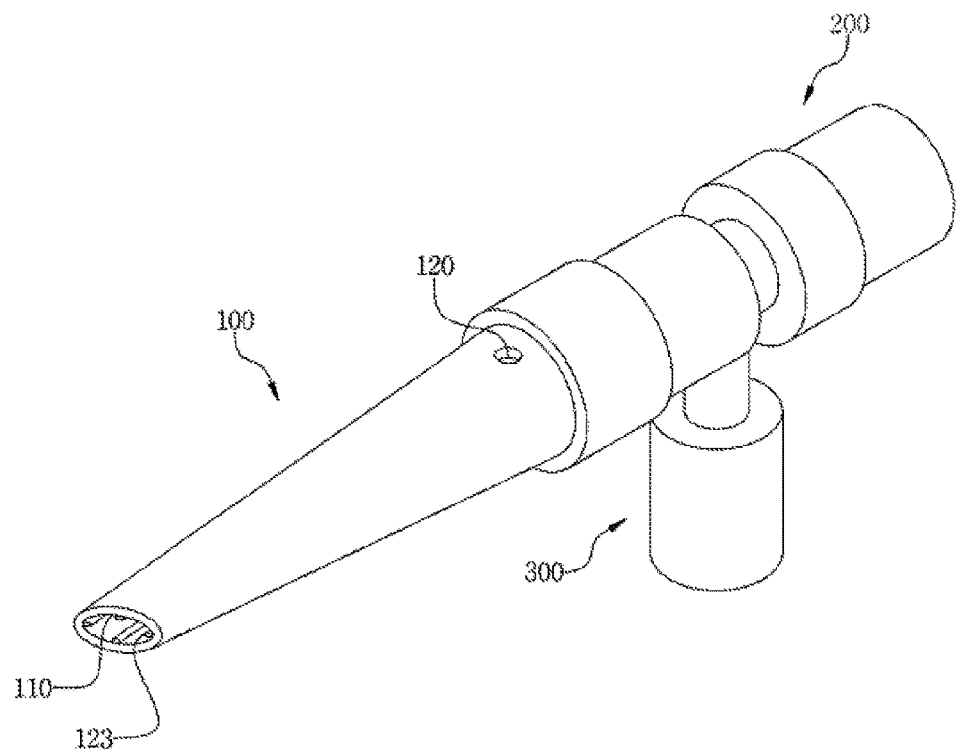
FIG. 5 is a perspective view illustrating a third embodiment of a mobile colposcopy device for early diagnosis of cervical cancer.
Figure 6:
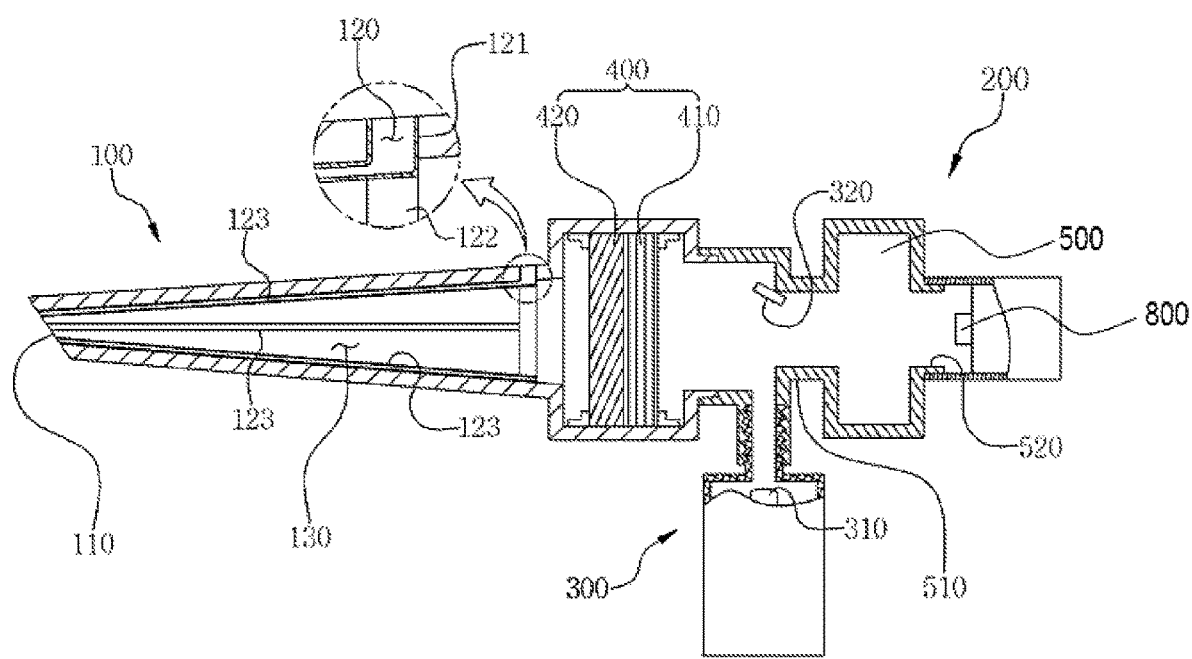
FIG. 6 is a cross-sectional view illustrating an internal structure of the mobile colposcopy device for early diagnosis of cervical cancer of FIG. 5.

Meanwhile, FIGS. 5 to 6 illustrate a mobile colposcopy device 10 for early diagnosis of cervical cancer according to a third embodiment.

Elements having the same function as the drawings illustrated above are denoted by the same reference numerals.

Referring to FIGS. 5 and 6, the capturing unit 200 is provided at the rear end of the insertion unit 100 facing the penetrating hole 110 and includes a hyperspectral camera 800 facing the penetrating hole 110 and an optical coupler 500 provided between the hyperspectral camera 800 and the insertion unit 100.

The optical coupler 500 adjusts the focus of the hyperspectral camera 800 as a connection part including a lens so that an image of the cervix accurately focuses on an image sensor of the hyperspectral camera 800.

The hyperspectral camera 800 acquires many pictures having the same vision with respect to light having different wavelengths. During the screening of the cervix, when acetic acid is applied to the cervix, disordered regions are changed to white color. The reason is that light with any special wavelength is less reflected due to the application of acetic acid and light with any special wavelength is more reflected.

Since a blue-colored object absorbs light with colors other than blue and reflects blue light, our eyes or a camera recognizes the object as blue. If the color is changed to red by a certain operation, it is meant that a degree to be reflected and absorbed for each wavelength is changed. Since existing cameras have only three pixels of RGB, the existing cameras can not accurately analyze a response of the cervix to light with various wavelengths.

However, for example, when there is a hyperspectral camera 800 capable of capturing images for 16 wavelengths, it is possible to more precisely analyze a color change and obtain more information. On the other hand, it is possible to indirectly measure concentrations of various light absorbers on the cervix using an image for each wavelength of the hyperspectral camera 800. That is, when there are many light absorbers absorbing well light with a specific wavelength, the light with the wavelength is reflected so that the amount returning to the camera is reduced (Beer-Lambert Law). Since an absorption spectrum of the light absorbers mainly distributed to the human body is well known, in the response to light with a plurality of wavelengths, it is possible to measure whether a certain absorber is present at a certain degree of concentration.

Accordingly, the hyperspectral camera 800 is used to acquire more disease information than a general camera.

The optical coupler 500 may adjust the focus according to a depth of the cervix varied for each person. Further, an end 510 of the optical coupler 500 may be connected and fixed to the insertion unit 100 and the other end 520 of the optical coupler 500 may also be connected to the hyperspectral camera 800 by facing a connection portion 510 of the insertion unit 100, thereby easily detaching the camera using a quick coupler.

Figure 7:
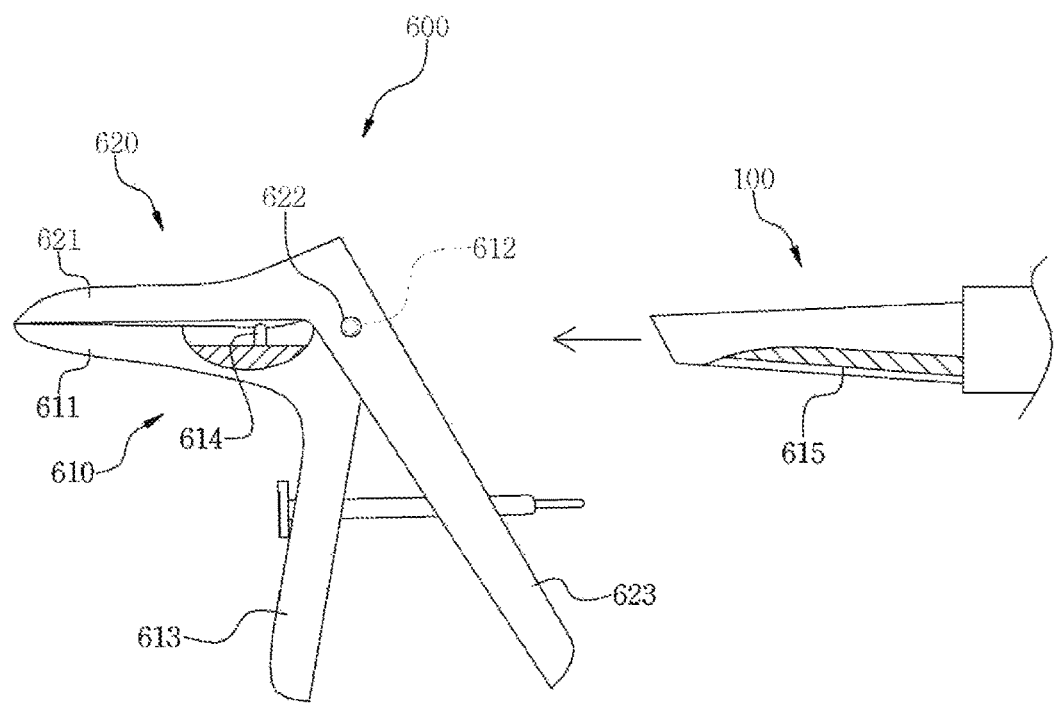
FIG. 7 is a schematic view of a mobile colposcopy device for early diagnosis of cervical cancer including an extension unit.

FIG. 7 illustrates a mobile colposcopy device 10 for early diagnosis of cervical cancer according to yet another embodiment of the present disclosure.

Elements having the same function as the drawings illustrated above are denoted by the same reference numerals.

Referring to FIG. 7, the mobile colposcopy device 10 for early diagnosis of cervical cancer in which an extension unit 600 is further included in the insertion unit 100 further includes the extension unit 600 provided in the insertion unit 100.

The extension unit 600 extends a space in the vagina when the insertion unit 100 is inserted into the vagina, has a hollow so that an end of the insertion unit 100 may be inserted, and includes a first extension member 610 and a second extension member 620.

The first extension member 610 includes a first body 611 extended in a predetermined length forward and backward, a first bracket 612 extended backward in the second half, and a first handle 613 extended in a predetermined length downward from the first bracket 612.

The second extension member 620 includes a second body 621 extended in a predetermined length forward and backward, a second bracket 622 at a rear end to be rotatable on the first bracket 612, and a second handle 623 extended in a predetermined length downward from the second bracket 622.

The first handle 613 and the second handle 623 are held by an operator to rotate the first extension member 610 and the second extension member 620.

A guide protrusion 614 is formed on an upper end of the first body 611, the insertion unit 100 has a guide groove 615 extended in a predetermined length along an insertion direction to the vagina, that is, forward and backward, and the guide protrusion 614 is inserted to the guide groove 615.

In the present embodiment, the guide protrusion 614 protrudes upward from an upper surface of the first body 611, but is not limited thereto, and may also be formed on a lower surface of the second body 621.

Accordingly, the first extension member 610 and the second extension member 620 are supported to each other to be rotatable with each other so that be far from the center of the hollow.

Figure 8:
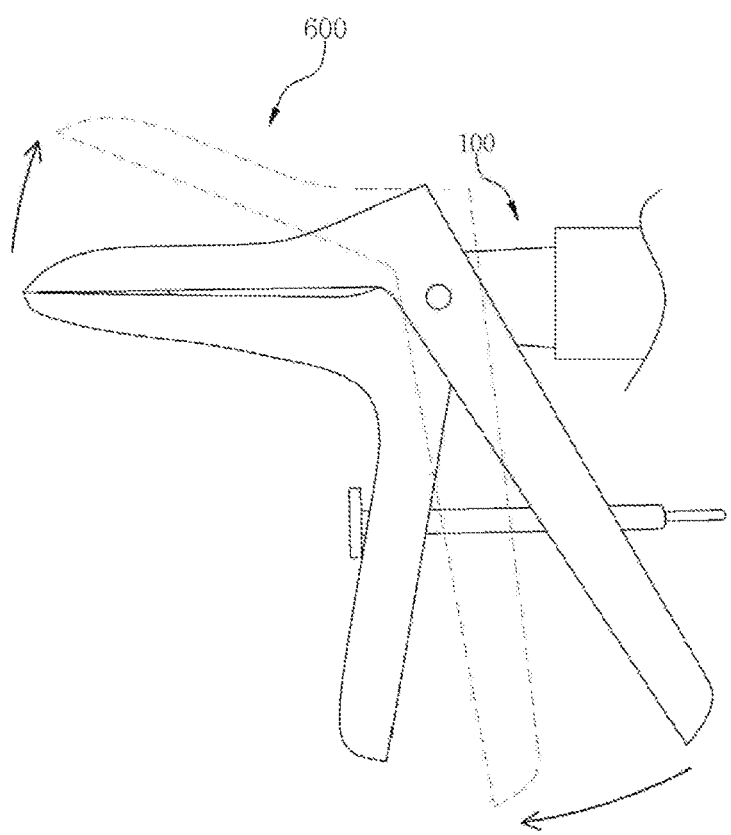
FIG. 8 is an operational view illustrating an operation of the extension unit of FIG. 7.

Referring to FIG. 8, an operation of the extension unit 600 will be described in detail as follow.

When the guide protrusion 614 moves toward the penetrating hole 110 along the guide groove 615, the extension unit 600 is inserted into the vagina earlier than the insertion unit 100, and when the insertion unit 100 is inserted into the vagina, the guide protrusion 614 moves toward the capturing unit 200 along the moving direction of the guide groove 615 to capture the cervix.

Figure 10:
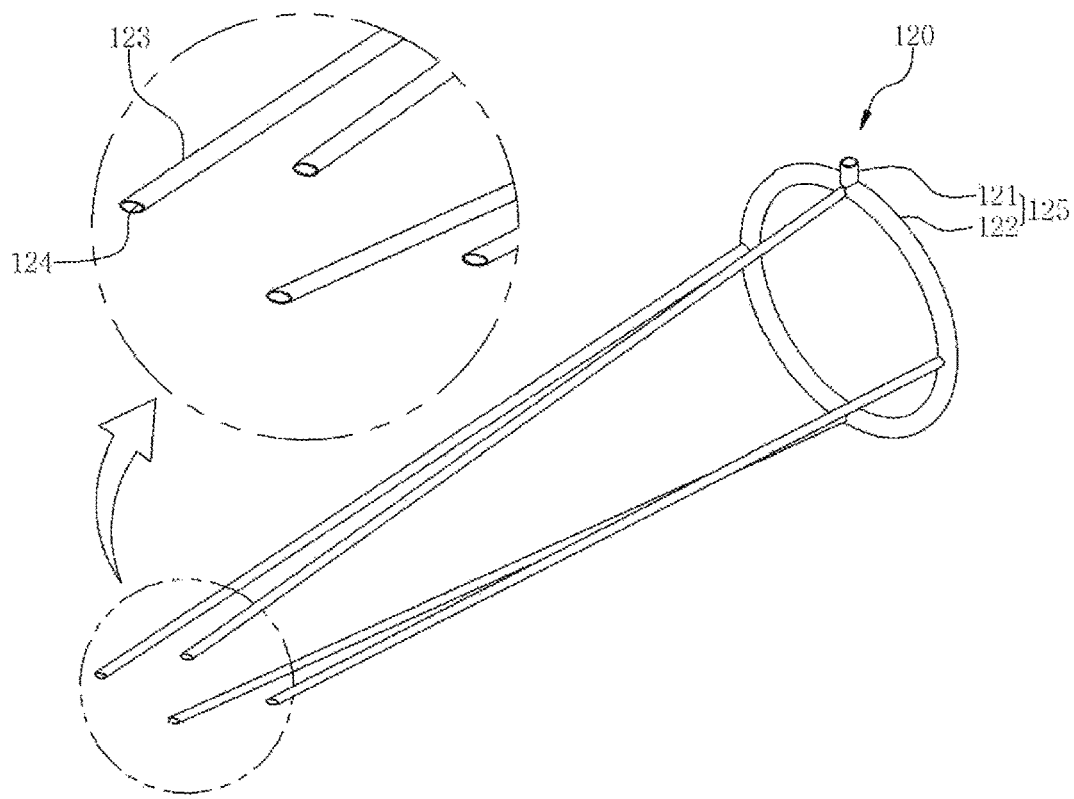
FIG. 10 is a perspective view illustrating yet another embodiment of an inlet of the mobile colposcopy device for early diagnosis of cervical cancer.
Figure 11:
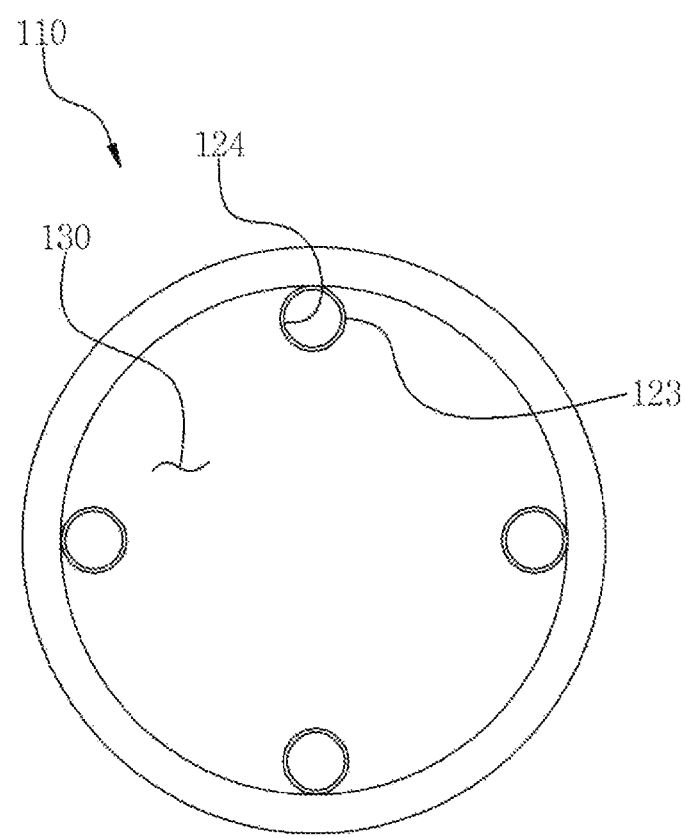
FIG. 11 is a cross-sectional view illustrating a cross section of a penetrating hole of the mobile colposcopy device for early diagnosis of cervical cancer of FIG. 10.

FIGS. 10 to 11 illustrate the inlet 120 of the mobile colposcopy device 10 for early diagnosis of cervical cancer according to yet another embodiment of the present disclosure.

Elements having the same function as the drawings illustrated above are denoted by the same reference numerals.

Referring to FIG. 10, the insertion unit 100 further includes a communication unit 125 and an ejection pipe 123.

The communication unit 125 includes a main pipe 121 and an auxiliary pipe 122.

The main pipe 121 is extended in a predetermined length to communicate with the inlet 120.

The auxiliary pipe 122 is extended from the main pipe 121, but formed in a circumferential direction along an inner circumferential direction of the insertion unit 100.

The ejection pipe 123 is extended to the penetrating hole 110 side along the capturing path 130 from the auxiliary pipe 122 and has at least one outlet 124 so that external air introduced through the inlet 120 is ejected to an end of the penetrating hole 110 or a test solution may be ejected to the penetrating hole 110 side.

Therefore, the test solution such as acetic acid is injected into the inlet 120 to be evenly applied on the cervix.

Referring to FIG. 11, a cross-sectional view of the penetrating hole 110 with a plurality of ejection pipes 123 is illustrated.

In the embodiment, four ejection pipes 123 are exemplified, but the number and the position thereof are not limited.

As described above, the mobile colposcopy device 10 for early diagnosis of cervical cancer of the present disclosure may simply cervical cancer screening using a mobile colposcopy without environmental constraints including hospitals, thereby more simply allowing women to early diagnose cervical cancer.

The description of the presented embodiments is provided so that those skilled in the art of the present disclosure use or implement the present disclosure. Various modifications of the embodiments will be apparent to those skilled in the art and general principles defined herein can be applied to other embodiments without departing from the scope of the present disclosure. Therefore, the present disclosure is not limited to the exemplary embodiments presented herein, but should be analyzed within the widest range which is coherent with the principles and new features presented herein.

What is claimed is:

1. A mobile colposcopy device for early diagnosis of cervical cancer comprising:
    an insertion unit configured to be inserted into a vagina of a woman, having a truncated cone shape, and comprising a first end having a penetrating hole configured to come into contact with a uterus, and a capturing path configured to communicate with the penetrating hole;
    a capturing unit configured to capture an image of a cervix through the capturing path of the insertion unit; and
    a lighting unit positioned between the insertion unit and the capturing unit, and configured to irradiate light toward the cervix through the penetrating hole of the insertion unit,
    wherein the insertion unit comprises:
        an inlet positioned an upper surface of the insertion unit, and configured to circulate air in the capturing path to an outside the mobile colposcopy device, and inject a test solution to the cervix;
        an auxiliary pipe having a ring shape positioned along an inner circumferential surface of the insertion unit;
        a main pipe connecting the inlet and the auxiliary pipe; and
        a plurality of ejection pipes, each of which is extended toward the penetrating hole along the capturing path from the auxiliary pipe, and has an outlet configured to eject, through the penetrating hole, external air introduced through the inlet, or the test solution introduced through the inlet.

2. The mobile colposcopy device of claim 1, wherein the lighting unit includes a light source configured to irradiate the light on the capturing path; and a light guide which induces the light generated in the light source in a direction of the penetrating hole.

3. The mobile colposcopy device of claim 1, further comprising:
    an optical unit positioned on the capturing path and configured to block reflection light which is reflected on a surface of a cervical tissue to be introduced to the penetrating hole, and transmit only a lighting which is reflected to the penetrating hole from an inside of the cervical tissue by passing through the surface of the cervical tissue.

4. The mobile colposcopy device of claim 1, wherein the capturing unit is configured to hold a smartphone having a capturing camera, and support the smartphone so that the capturing camera faces the penetrating hole and captures the cervix through the penetrating hole.

5. The mobile colposcopy device of claim 4, wherein an insertion space is provided at a second end of the insertion unit and formed so that the smartphone is inserted, but formed with a setting port in which a capturing lens of the capturing camera is set at a position facing the penetrating hole.

6. The mobile colposcopy device of claim 3, wherein the capturing unit is any one of an endoscope camera and a hyperspectral camera.

7. The mobile colposcopy device of claim 1, wherein the penetrating hole is inclined at a predetermined angle based on a longitudinal center line of the capturing path.

8. The mobile colposcopy device of claim 1, further comprising:
    an extension unit which extends a space in the vagina when the insertion unit is inserted into the vagina.

9. The mobile colposcopy device of claim 8, wherein the extension unit has a hollow so that an end of the insertion unit may be inserted, but includes a first extension member and a second extension member which are supported to each other to be rotatable with each other so that it may be far from a center of the hollow; and a plurality of handles which are formed in the extension unit and configured to be held by an operator, to rotate the first and second extension members.

10. The mobile colposcopy device of claim 9, wherein the insertion unit has a guide groove extended in a predetermined length along an insertion direction to the vagina, and the extension unit has a guide protrusion formed on any one of the first extension member and the second extension member so as to be inserted to the guide groove.

11. The mobile colposcopy device of claim 1, wherein the insertion unit has an inner diameter which is tapered to be closer to the penetrating hole so that scattering light output from the lighting unit and scattered by an inner wall surface is incident to a cervical tissue.

12. The mobile colposcopy device of claim 4, wherein the optical unit consists of a linear polarizer (LP) which is provided on the capturing path and forms a parallel polarization (P-polarization) of light output from the lighting unit and a 1/4λ retarder (QWP) which is provided behind the linear polarizer based on an output direction of the light on the capturing path to form light passing through the linear polarizer to a left circular polarization.

* * * * *